United States Patent [19]

McNeill

[11] Patent Number: 5,633,151
[45] Date of Patent: May 27, 1997

[54] ENZYMATIC PROCESS FOR THE ISOLATION OF ERUCIC ACID FROM VEGETABLE OILS

[75] Inventor: Gerald P. McNeill, Glenside, Pa.

[73] Assignee: The United States of America as represented by the Secretary of Agriculture, Washington, D.C.

[21] Appl. No.: 406,829

[22] Filed: Mar. 20, 1995

Related U.S. Application Data

[63] Continuation of Ser. No. 334,089, Nov. 4, 1994.

[51] Int. Cl.⁶ ............ C12P 7/40; C12P 7/64; C12N 9/20
[52] U.S. Cl. .......... 435/134; 435/135; 435/136; 435/198
[58] Field of Search .......... 435/134, 136, 435/135, 198

[56] References Cited

U.S. PATENT DOCUMENTS 5,288,619  2/1994  Brown et al. .......... 435/134
5,370,996  12/1994  Metz et al. .......... 435/134

OTHER PUBLICATIONS

Baillargeon et al Biotech Letters vol. 13 No. 12 871–4(1991).
Sonnet et al Jaocs vol. 70(4) 387–391 Apr. 1993.
Trani et al Jaocs vol. 70(10) 961–4 Oct. 1993.
Hoshino et al., *Agric. Biol. Chem.*, vol. 54(6), pp. 1459–1467 (1990).
Kaimal et al., *Biotechnology Letters*, vol. 15(4), pp. 353–356 (1993).
Ergan et al., *Annals N.Y. Acad. of Sci.*, vol. 672, pp. 37–44 (1992).

*Primary Examiner*—Herbert J. Lilling
*Attorney, Agent, or Firm*—M. Howard Silverstein; John Fado; Janelle S. Graeter

[57] ABSTRACT

Erucic acid is produced by enzymatic hydrolysis, the reaction being catalyzed by lipase from *Geotrichum candidum* or *Candida rugosa*. Fatty acid substituents having carbon chains shorter than C22 are removed from triglycerides which also contain one or two erucic acid substituents, resulting in a glyceride fraction enriched in erucic acid and a free fatty acid fraction containing the hydrolyzed substituent.

10 Claims, 3 Drawing Sheets

ENZYMATIC PROCESS FOR THE ISOLATION OF ERUCIC ACID FROM VEGETABLE OILS

This application is a continuation of application Ser. No. 08/334,089, filed Nov. 4, 1994.

BACKGROUND OF THE INVENTION

1. Field of the Invention

Erucic acid is a fatty acid which is an important raw material in the oleochemical industry. It is a component of several vegetable oils, the major industrial source of erucic acid at present being high erucic acid rapeseed oil (HEAR oil). Current methods of extraction are costly, however, and the finished product contains by-products which impart undesirable properties. Thus, there is a need for an effective, low cost method of extraction which results in the production of a high-quality product.

2. Description of the Prior Art

Erucic acid (C22:1,δ13) is a naturally-occurring fatty acid found in the storage triglycerides of plants of the family Brassicaceae. Rapeseed is a member of this family and is grown in several countries for its oilseed. Rapeseed oil contains a high content of erucic acid (more than 40%) and is important in industrial applications.

Erucic acid can be isolated from rapeseed oil fatty acids by fractional distillation or multiple solvent crystallization at low temperature (Stage, H., *Fette Seifen Anstrichm.* 1975. vol. 77, p. 165–204). In the case of fractional distillation, however, temperatures of up to 255° C. must be utilized which may result in by-product formation which imparts an undesirable color to the erucic acid (Stage, H., *World Conference on Oleochemicals into the 21st Century.* T. H. Applewhite, ed. 1990. American Oil Chemists Society, pp. 142–160).

The search has thus continued for a process for purifying erucic acid from vegetable oils under mild hydrolysis conditions which result in a high-quality product of high yield and high purity.

It was found that lipases having fatty acid selectivity provided a milder, more convenient route to erucic acid production. Lipase from *Geotrichum candidum* (*G. candidum*), well known for its preference for C18 fatty acids containing a cis double bond in the δ9 position (Jensen, R. G., *Lipids.* 1974. vol. 9, pp. 149–157), poorly utilizes fatty acids which are longer than 18 carbons even if a cis double bond is located at the δ9 position in the fatty acid chain (Sonnet et al., *J. Am. Oil Chem. Soc.* 1993. vol. 70, pp. 1043–1045).

Lipase from *Candida rugosa* (*C. rugosa*) also exhibits some fatty acid selectivity, releasing long chain fatty acids more slowly than C16 and C18 acids from fish oil triglycerides (Lie and Lambertson, *Fette Seifen Anstrichm.* 1986. vol. 88, pp. 365–367; Hoshino et al., *Agric. Biol. Chem.* 1990. vol. 54, pp. 1459–1467). In addition, it was recently found that this enzyme hydrolyses esters containing erucic acid more slowly than those containing C16 or C18 fatty acids (Sonnet, supra; Ergan et al., *Annal. N.Y. Acad. Sci.* 1992. vol. 672, pp. 37–44; Kaimal et al., *Biotech. Lett.* 1993. vol. 15, pp. 353–356). Most fatty acids in rapeseed oil are either C18 or erucic acid. Hydrolysis of rapeseed oil with this lipase should thus result in a glyceride fraction enriched in erucic acid and a free fatty acid fraction containing only C18 acids. These fractions can be easily separated from each other, thus providing a fraction containing a mixture of the glycerides mono- and dierucin. The limited specificity of this lipase is insufficient for a commercially useful process, however, therefore studies were carried out to determine a means of enhancing the process.

SUMMARY OF THE INVENTION

I have discovered that erucic acid may be produced by enzymatic hydrolysis utilizing lipases from *Geotrichum candidum* or *Candida rugosa* to catalyze the reaction. Fatty acid substituents with carbon chains shorter than C22 are removed from triglycerides which also contain one or two erucic acid substituents, resulting in a glyceride fraction enriched in erucic acid and a free fatty acid fraction containing the hydrolyzed substituent. The reaction utilizing lipase from *C. rugosa* is temperature-sensitive, requiring a reaction temperature of less than 20° C. for the procedure to be effective. When using HEAR oil as the source of erucic acid, the glyceride fraction is enriched to approximately 85% compared to 50% in the raw material when utilizing lipase from *G. candidum*. Little or no erucic acid is found in the free fatty acid fraction. The glyceride fraction is enriched with erucic acid to approximately 95% when utilizing lipase from *C. rugosa*, with approximately 10% appearing in the free fatty acid fraction.

In accordance with this discovery it is an object of the invention to provide a novel method for producing erucic acid by enzymatic hydrolysis in a two-phase, water/oil reaction system, utilizing lipase from either *G. candidum* or *C. rugosa* to catalyze the reaction.

Other objects and advantages will become readily apparent from the following description.

DETAILED DESCRIPTION OF THE INVENTION

Initially, studies were carried out to compare the ability of three lipases to hydrolyze high erucic acid rapeseed oil (HEAR oil), with the objective of concentrating the erucic acid in a single glyceride fraction. Lipases from *Pseudomonas cepacia* (*P. cepacia*), *G. candidum* and *C. rugosa* were considered, and the effects of time, temperature, water content and enzyme concentration were evaluated.

Figure 1A:
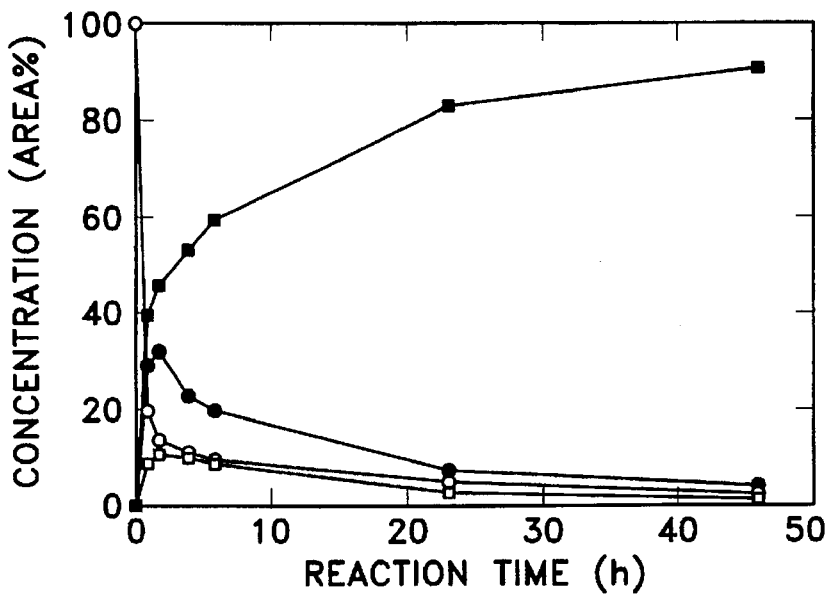
FIG. 1 shows the change in composition of glycerides and free fatty acids during lipase catalyzed hydrolysis of HEAR oil at 35° C. for *Pseudomonas cepacia* (panel A), *Candida rugosa* (panel B), *Geotrichum candidum* (C).

In time course of hydrolysis studies carried out at 35° C., lipase from *P. cepacia* was found to release all fatty acids rapidly and did not result in selective distribution of erucic acid. This non-specific lipase almost completely hydrolyzed the triglyceride to free fatty acid in 48 hours (FIG. 1a). Both monoglycerides and diglycerides appeared as intermediates, reaching a maximum of 35% and 10%, respectively, after 2 hours, and were almost completely hydrolyzed after 48 hours.

Figure 1B:
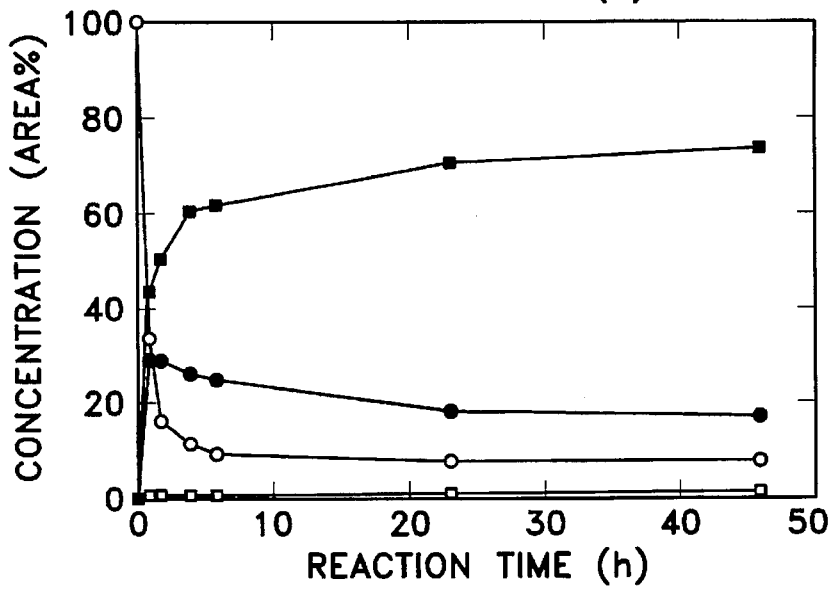

Lipase from *C. rugosa* released erucic acid more slowly than C18 and 20 fatty acids at 35° C. but only resulted in a limited accumulation of the erucic acid in the di- and triglyceride fractions. Hydrolysis using the *C. rugosa* lipase occurred in two stages (FIG. 1b): a fast release of free fatty acids up to 6 hours reaction time, reaching a level of 60%, and a slow release between 6 and 48 hours, reaching a final concentration of 75%. Decrease in diglyceride concentration was slow compared to that with *P. cepacia* lipase. After 48 hours reaction time, the hydrolysis of diglycerides was not complete.

*G. candidum* lipase released C20 and C22 fatty acids extremely slowly at 35° C., resulting in their accumulation in the di- and triglyceride fractions. Less than 2% of the total erucic acid was found in the free fatty acid fraction. Diglyceride concentration reached 45% after 4 hours reaction time and in contrast to the other lipases no hydrolysis of diglyceride occurred beyond this time. A maximum free fatty acid level of 50% was reached, and monoglyceride levels were almost zero throughout the reaction.

Figure 1C:
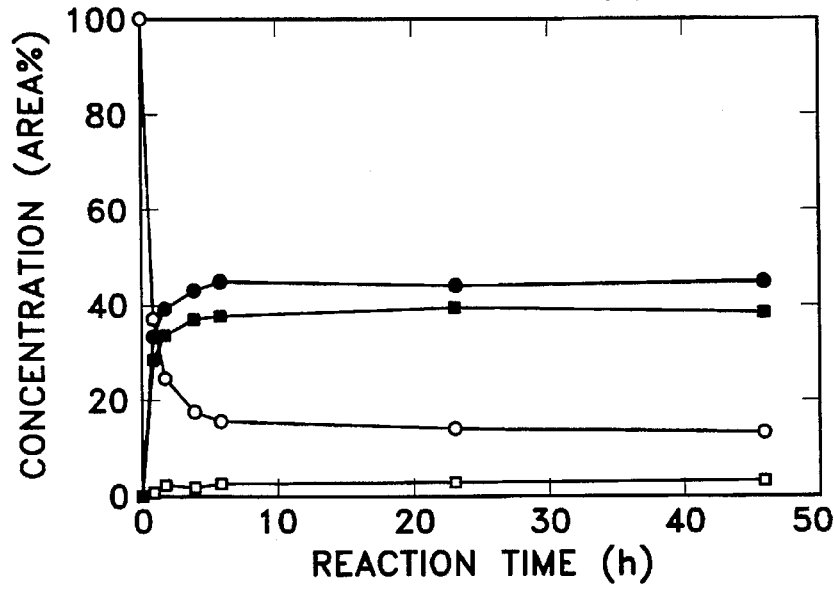

A detailed composition of the reaction mixture during hydrolysis of HEAR oil (as shown in FIG. 1) after 4 hours and 24 hours reaction time at 35° C. is shown in Table I. After 4 hours hydrolysis with *P. cepacia* lipase, the major diglyceride species was C40, corresponding to 1 molecule of erucic acid and 1 molecule of C18 acid bound to glycerol. Triglycerides containing erucic acid (e.g. C60) were hydrolyzed extensively and the major free fatty acid was erucic acid (C22). At 24 hours, release of more than 85% fatty acids had occurred. The relative proportions of the individual free fatty acids is consistent with a non-specific hydrolysis.

The composition of the reaction mixture after 4 hours hydrolysis using *C. rugosa* lipase is clearly different from that of *P. cepacia* lipase. The major diglyceride was dierucin (C44) and the concentration of C18 free fatty acid was almost three times greater than C22 free fatty acid. The C22 free fatty acid concentration had increased to approximately 23% after 24 hours reaction time with a corresponding decrease in C44 diglyceride.

TABLE 1

Composition of the Reaction Mixture (area %) after 4 h and 24 h Reaction Time during Lipase-catalysed Hydrolysis of HEAR Oil at 35° C.

| Acyl Carbon No. | HEAR oil | *P. cepacia* 4 h | *P. cepacia* 24 h | *C. rugosa* 4 h | *C. rugosa* 24 h | *G. candidum* 4 h | *G. candidum* 24 h |
|---|---|---|---|---|---|---|---|
| FFA | | | | | | | |
| c16 | 0.0 | 2.5 | 3.1 | 3.7 | 3.5 | 3.3 | 3.2 |
| c18 | 0.0 | 16.9 | 32.6 | 39.0 | 37.5 | 35.2 | 34.1 |
| c20 | 0.0 | 6.1 | 8.5 | 5.0 | 7.8 | 0.0 | 0.8 |
| c22 | 0.5 | 28.4 | 39.9 | 13.8 | 23.3 | 0.7 | 0.8 |
| MG | | | | | | | |
| c18 | 0.0 | 5.1 | 1.6 | 0.6 | 0.8 | 0.5 | 0.0 |
| c20 | 0.0 | 0.8 | 0.0 | 0.1 | 0.2 | 0.0 | 0.0 |
| c22 | 0.0 | 4.1 | 1.2 | 0.3 | 0.3 | 2.2 | 2.4 |
| DG | | | | | | | |
| c34 | 0.0 | 0.0 | 0.0 | 0.0 | 0.0 | 0.0 | 0.0 |
| c36 | 0.0 | 4.1 | 1.5 | 0.0 | 0.2 | 0.0 | 0.0 |
| c38 | 0.0 | 2.7 | 0.8 | 0.0 | 0.2 | 2.0 | 1.5 |
| c40 | 0.6 | 10.7 | 3.4 | 1.4 | 0.8 | 6.3 | 6.4 |
| c42 | 0.0 | 1.7 | 0.6 | 6.1 | 1.9 | 9.6 | 9.9 |
| c44 | 0.0 | 3.5 | 1.3 | 18.2 | 13.9 | 24.4 | 26.2 |
| c46 | 0.0 | 0.0 | 0.0 | 1.1 | 0.8 | 0.8 | 1.0 |
| TG | | | | | | | |

TABLE 1-continued

Composition of the Reaction Mixture (area %) after 4 h and 24 h Reaction Time during Lipase-catalysed Hydrolysis of HEAR Oil at 35° C.

| Acyl Carbon No. | HEAR oil | *P. cepacia* 4 h | *P. cepacia* 24 h | *C. rugosa* 4 h | *C. rugosa* 24 h | *G. candidum* 4 h | *G. candidum* 24 h |
|---|---|---|---|---|---|---|---|
| c52 | 2.7 | 0.4 | 0.0 | 0.0 | 0.0 | 0.0 | 0.0 |
| c54 | 8.8 | 1.3 | 0.8 | 0.0 | 0.2 | 0.0 | 0.0 |
| c56 | 9.3 | 1.6 | 0.7 | 0.0 | 0.2 | 0.9 | 0.7 |
| c58 | 10.4 | 3.9 | 2.0 | 1.4 | 0.7 | 2.3 | 2.0 |
| c60 | 19.4 | 1.5 | 0.8 | 3.7 | 1.7 | 4.5 | 3.7 |
| c62 | 46.3 | 3.1 | 1.3 | 7.3 | 5.2 | 10.1 | 7.3 |
| c64 | 1.9 | 0.0 | 0.0 | 0.1 | 0.8 | 0.6 | 0.0 |
| c64 | 0.0 | 0.0 | 0.2 | 0.0 | 0.0 | 0.0 | 0.0 |

After 4 hours hydrolysis using lipase from *G. candidum*, diglyceride containing C20 or C22 fatty acids (C40, C42 and C44) had reached a higher level than occurred in the reaction with *P. cepacia* or *C. rugosa* lipases. At 24 hours reaction time, the concentration of these diglycerides had increased slightly and approximately 13% of triglycerides remained unhydrolysed. These triglycerides were mainly C58, C60 and C62, each of which must contain 2 or 3 molecules of C20 or C22 fatty acids. In the free fatty acid fraction, the concentration of C20 and C22 fatty acids never exceeded 1% of total reaction mixture throughout the reaction period.

In order to optimize the partial fatty acid hydrolysis selectivity toward C22 fatty acids observed with *C. rugosa* lipase, the effects of external parameters such as temperature, initial water concentration and enzyme concentration were investigated. To determine the effects of temperature, hydrolysis of HEAR oil was carried out at 35°, 20°, 15°, and 10° C. At 15° and 10° C., the reaction mixture became cloudy after 20 minutes reaction time and after 2 hours was a soft solid. The reaction proceeded, although stirring was no longer possible. At 35° C. no cloudiness or solidification occurred, but at 20° C. the reaction mixture was cloudy and viscous after 2 hours.

Figure 2A:
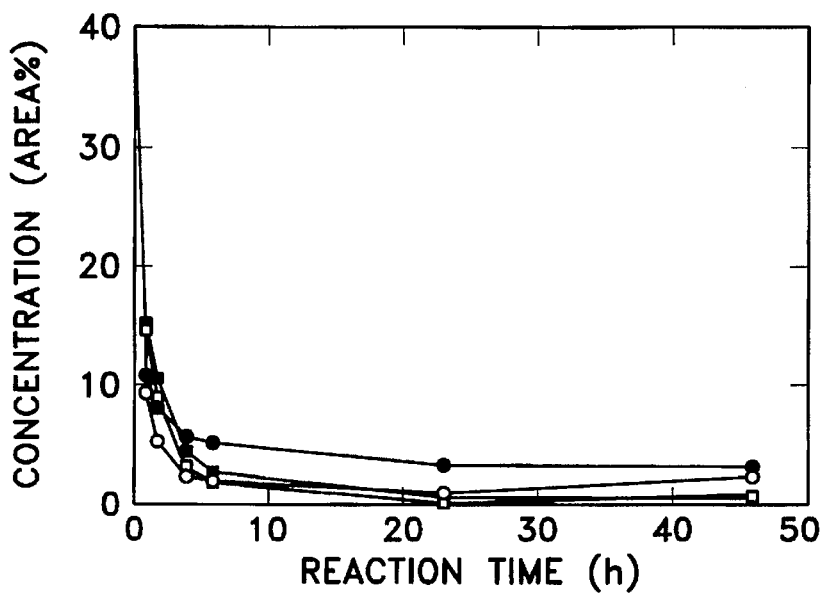
FIG. 2 shows the change in concentration of glycerides and free fatty acids during hydrolysis of HEAR oil using *Candida rugosa* lipase at different temperatures. Panel A shows C62 triglyceride concentrations, panel B shows C44 diglyceride concentrations, panel C shows C22 free fatty acid concentrations.

In FIG. 2, the appearance of selected products and disappearance of selected triglycerides during the course of the reaction at different temperatures is compared. The decrease in concentration of the C62 triglyceride (FIG. 2a) was similar at all temperatures but complete hydrolysis did not occur at 35° C.

Figure 2B:
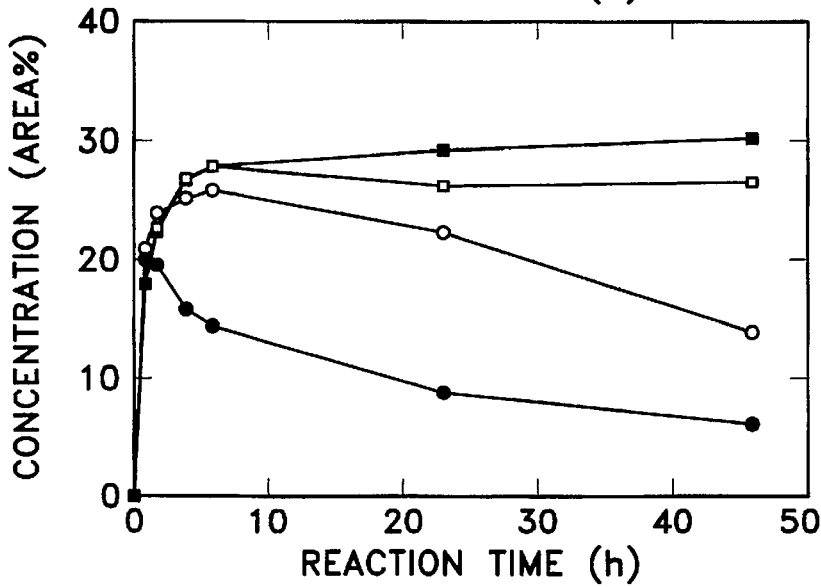

The concentration of C44 diglyceride (dierucin), as shown in FIG. 2b, increased at all temperatures during the first hour of reaction, but thereafter exhibited a strong temperature dependent variation. At 20° C. and 15° C., a level of approximately 30% was reached after 6 hours. At 10° C. this level remained constant throughout the reaction, but at 15° C. it decreased slightly. At 35° C. the C44 concentration peaked at 20% after 2 hours reaction, then steadily decreased to 5% after 48 hours. Reaction at 20° C. was intermediate, with a maximum C44 diglyceride concentration of 27% after 6 hours which gradually decreased to 14% after 48 hours.

Figure 2C:
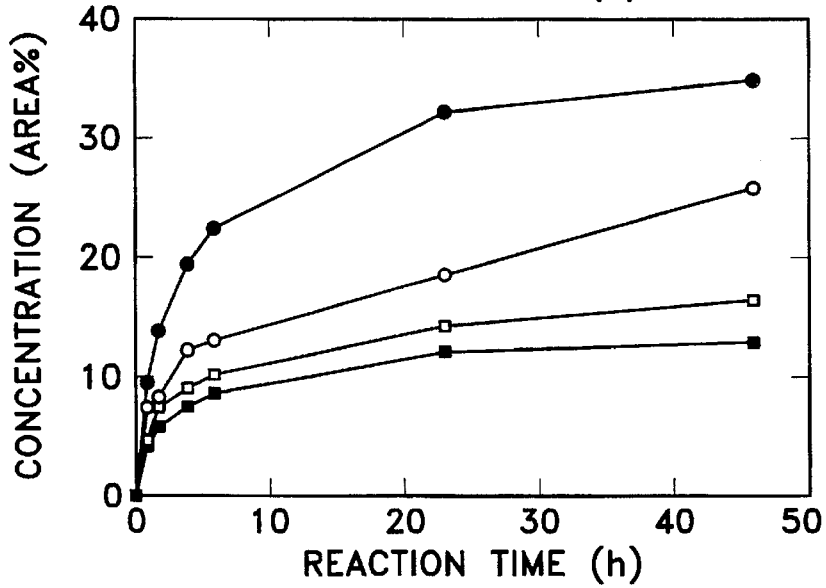

The production and final concentration of free erucic acid (C22) was also strongly temperature dependent (FIG. 2c). The final concentration of C22 was lower at the lower temperatures At 20° and 35° C. the relatively large increase in C22 between 6 and 48 hours reaction time corresponds to the decrease in concentration of C44 diglyceride. A small increase in C22 concentration at 10° C. during this period may be caused by the decrease in the C62 triglyceride concentration as shown in FIG. 1a.

Hydrolysis of HEAR oil by *C. rugosa* lipase at 10° C. was repeated four times and the composition of the reaction mixture after 48 hours was determined by gas chromatography and used to calculate the mean and standard deviation for the major glycerides and free fatty acids (area %±SD):

free fatty acids
C16=3.8±0.2
C18=39.3±0.6
C20=7.7±0.5
C22=12.6±0.5
monoglycerides
C18=0.8±0.1
C20=0.2±0.1
C22=0.1±0.1
diglycerides
C38=0.3±0.1
C40=0.4±0.1
C42=3.6±0.3
C44=29.7±0.7
C46=1.0±0.1
triglycerides
C58=0.1±0.1
C60=0.3±0.1
C62=0.5±0.1.

Hydrolysis of HEAR oil by *P. cepacia* lipase was also carried out at 10° C. but no difference in the composition of the reaction mixture compared with reaction at 35° C. was observed after 48 hours (data not shown).

Water is present in the reaction mixture due to the requirement for dissolving the lipase before mixing it with the erucic acid-containing oil. In order to determine the minimum amount of water needed for the reaction to proceed, the hydrolysis of HEAR oil was carried out at 10° C. using *C. rugosa* lipase as catalyst where initial water concentrations of 2, 5, 9, 17, 30, 40 and 60 wt % were present in the reaction mixture. The composition of the reaction mixture after 48 hours is shown in Table 2. At the lowest water content investigated (2% water), hydrolysis of triglycerides was incomplete and the concentration of C44 diglycerides was relatively low (20%). At all other water concentrations, almost total hydrolysis of triglycerides was attained and a concentration of approximately 30% C44 diglyceride was observed. When the water content was less than 30%, the content of C36–C42 diglycerides and C10 monoglyceride was higher, while the content of C18 and C22 free fatty acid was correspondingly lower. The reaction mixture solidified at all concentrations. At the 60% water concentration, the reaction mixture was not homogenous; free aqueous phase was visible in pockets distributed around a semi-solid emulsion of oil and buffer.

TABLE 2

Effect of Water Content on the Composition of the Reaction Mixture (area %) after 24 h Hydrolysis of HEAR Oil (5 g) Using *Candida rugosa* Lipase (100 mg) at 10° C.

| Acyl Carbon No. | Added Water | | | | | | |
|---|---|---|---|---|---|---|---|
| | 2% | 5% | 9% | 17% | 30% | 40% | 60% |
| FFA | | | | | | | |
| c16 | 2.5 | 3.3 | 3.2 | 3.5 | 3.7 | 3.7 | 3.8 |
| c18 | 22.5 | 34.8 | 34.8 | 37.0 | 38.9 | 40.1 | 38.7 |
| c20 | 1.4 | 4.1 | 6.2 | 6.9 | 7.1 | 7.6 | 6.8 |
| c22 | 2.3 | 6.3 | 9.0 | 10.6 | 10.9 | 12.2 | 10.6 |
| MG | | | | | | | |

TABLE 2-continued

Effect of Water Content on the Composition of the Reaction Mixture (area %) after 24 h Hydrolysis of HEAR Oil (5 g) Using *Candida rugosa* Lipase (100 mg) at 10° C.

| Acyl Carbon No. | Added Water | | | | | | |
|---|---|---|---|---|---|---|---|
| | 2% | 5% | 9% | 17% | 30% | 40% | 60% |
| c18 | 1.2 | 1.3 | 1.7 | 1.2 | 1.6 | 0.6 | 0.4 |
| c20 | 0.2 | 0.0 | 0.2 | 0.1 | 0.1 | 0.2 | 0.1 |
| c22 | 0.6 | 0.4 | 0.3 | 0.2 | 0.0 | 0.0 | 0.2 |
| DG | | | | | | | |
| c34 | 0.5 | 0.0 | 0.3 | 0.3 | 0.0 | 0.0 | 0.0 |
| c36 | 2.2 | 2.1 | 1.1 | 0.7 | 0.2 | 0.2 | 0.0 |
| c38 | 2.4 | 1.4 | 1.0 | 0.8 | 0.4 | 0.4 | 0.4 |
| c40 | 3.6 | 1.4 | 1.2 | 1.0 | 0.5 | 0.5 | 0.5 |
| c42 | 5.7 | 7.7 | 5.0 | 4.2 | 4.2 | 4.2 | 4.4 |
| c44 | 17.5 | 31.3 | 32.2 | 30.6 | 30.5 | 29.4 | 32.3 |
| c46 | 0.1 | 1.1 | 1.1 | 1.5 | 2.2 | 0.7 | 1.7 |
| TG | | | | | | | |
| c52 | 0.5 | 0.0 | 0.0 | 0.0 | 0.0 | 0.0 | 0.0 |
| c54 | 1.7 | 0.0 | 0.4 | 0.1 | 0.0 | 0.0 | 0.0 |
| c56 | 2.6 | 0.0 | 0.3 | 0.1 | 0.0 | 0.0 | 0.0 |
| c58 | 3.9 | 0.0 | 0.4 | 0.2 | 0.1 | 0.0 | 0.0 |
| c60 | 8.3 | 1.5 | 0.6 | 0.4 | 0.2 | 0.4 | 0.2 |
| c62 | 20.1 | 3.0 | 0.8 | 0.6 | 0.0 | 0.6 | 0.0 |
| c64 | 0.0 | 0.0 | 0.2 | 0.0 | 0.0 | 0.0 | 0.0 |

Figure 3:
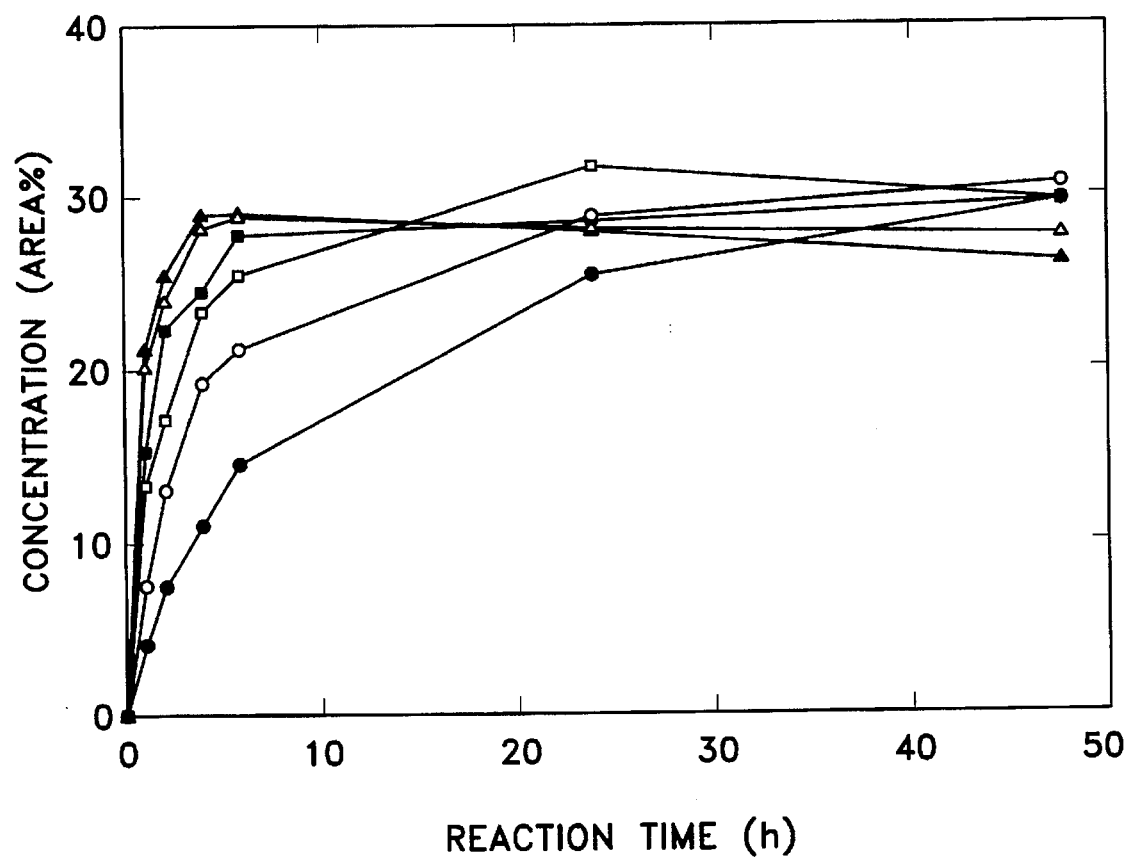
FIG. 3 shows the effect of concentration of *Candida rugosa* lipase on the production of C44 (dierucin) during hydrolysis of 5 g of HEAR oil at 10° C.

The hydrolysis of HEAR oil was carried out at 10° C. with increasing concentrations of *C. rugosa* lipase (from 10 mg to 400 mg). The rate of production of C44 diglyceride increased with increasing concentration as shown in FIG. 3. The rates for 200 mg and 400 mg, however, were almost identical under these particular conditions. At the higher enzyme concentrations, a small decrease in the C44 diglyceride concentration occurred between 24 and 48 hours reaction time. At all enzyme concentrations, a level of approximately 30% C44 diglyceride was reached within the 48-hour reaction period investigated.

Previous studies on the relative reactivity of fatty acids ranging from C16–C22 towards *P. cepacia* lipase had shown no enzyme selectivity against any particular acid (Sonnet, supra). Analysis of the reaction mixture during hydrolysis of HEAR oil confirmed this finding and showed that the major intermediate was a diglyceride containing one erucic acid molecule and one molecule of C18 fatty acid. Altering the reaction conditions had no effect on this breakdown patter, therefore this enzyme was eliminated as a candidate for use in a process for the purification of erucic acid from HEAR oil.

Lipase from *G. candidum*, on the other hand, was shown to be a useful candidate for this purpose. Although this lipase was well known for its ability to preferentially hydrolyze esters of cis δ9 unsaturated C18 fatty acids, compared to their saturated counterparts, it had also been shown (Sonnet, supra) that esters of unsaturated fatty acids longer than C18 were also hydrolyzed, though extremely slowly. HEAR oil hydrolysis using this enzyme resulted in almost no release of erucic acid with extensive release of C18 fatty acids, which in HEAR oil are mainly cis δ9 unsaturated. Most of the erucic acid was thus concentrated in the diglyceride fraction as dierucin (C44). In addition, almost no release of C20 fatty acids was observed, resulting in accumulation of these fatty acids in the diglyceride fraction also, but as non-C44 diglycerides. The overall result of the reaction occurs over a short period of time, and the accumulation of erucic acid in the diglyceride fraction reaches an approximately 85% concentration.

The similarity in the specificities of the lipases from *C. rugosa* and *G. candidum* is not surprising considering the close homology which has recently been demonstrated between these enzymes on the molecular level (Li et al., *J. Biol. Chem.* 1993. vol. 268, pp. 12843–12847). However, due to the relatively poor selectivity of the *C. rugosa* enzyme, erucic acid is poorly concentrated into the diglyceride fraction and a large amount of erucic acid is lost to the free fatty acid fraction at reaction temperatures of 35° and 20° C. Below 20° C., the accumulation of dierucin with the simultaneous solidification of the reaction mixture suggests that dierucin crystallizes as it is being produced. The solid becomes unavailable as a substrate to the enzyme thereby preventing further hydrolysis to free erucic acid. A similar phenomenon was previously observed during low temperature enzymatic glycerolysis of fats and oils where solidification of the reaction mixture with accumulation of monoglycerides was demonstrated to be caused by preferential crystallization of monoglyceride containing a saturated fatty acid (McNeill et al., *J. Am. Oil Chem. Soc.* 1992, vol. 69, pp. 1098–1103).

The result of dierucin crystallization is an accumulation of erucic acid in the diglyceride fraction at a higher purity than found with the more fatty acid selective *G. candidum* lipase, i.e. approximately 95%. In spite of the crystallization of dierucin, release of free erucic acid does occur at the early stages of the reaction, causing a loss of about 20% of total erucic acid to the free fatty acid fraction. Both *G. candidum* and *C. rugosa* lipases are suitable catalysts for the concentration of erucic acid in specific glyceride fractions during hydrolysis of HEAR oil. The choice of enzyme in a practical situation will depend on the required purity of erucic acid and the relative costs of the enzymes.

The procedure for the production of erucic acid is carried out by adding lipase dissolved in buffer to erucic acid-containing oil, with stirring. Any oil which contains an erucic acid component may be treated with lipase to produce erucic acid as a mono- or diglyceride. Suitable oils are those derived from plants of the Brassicaceae family, for example, rapeseed oil, mustard seed oil, nasturtium oil and crambe seed oil. Preferred are rapeseed oil, mustard seed oil and crambe seed oil. Particularly preferred is high erucic acid rapeseed (HEAR) oil.

Effective concentrations of lipase have been found to range from about 0.2 wt % to about 8.0 wt %. Effective lipases are those isolated from *Geotricum candidum* and *Candida rugosa* and are available commercially, such as from Enzeco, New York, N.Y. Preferred concentrations of lipase are about 0.2 wt % to about 2.0 wt %. Particularly preferred is about 0.2 wt %.

The enzyme is dissolved in either water or any buffer which is conventionally used in carrying out enzymatic reactions at a pH of about 7.0. Examples are phosphate or Tris buffers. The enzyme is dissolved in buffer such that the water concentration in the reaction mixture is at least about 5 wt %.

The hydrolysis reaction should be carried out at a constant temperature, and the temperature used depends upon the choice of enzyme. Lipase from *G. candidum* is effective at temperatures of about 10° C. to about 35° C. Preferred temperatures are from about 20° C. to about 35° C., while particularly preferred is about 35° C. Lipase from *C. rugosa* is effective at temperatures of about 10° C. to about 20° C. Preferred temperatures are from about 10° C. to about 15° C., while particularly preferred is about 10° C.

The hydrolysis reaction can be carried out up to about 48 hours, however, within about 2 hours, erucic acid-containing glycerides will begin to appear in significant concentrations. As a general rule, higher enzyme concentrations will result in faster accumulation of end product.

Following the hydrolysis procedure, the glyceride fraction is separated from the free fatty acid fraction by any conventional method known and used in the art. For example, glyceride may be extracted from the reaction mixture with acetone, followed by crystallization. This procedure is carried out by warming the reaction mixture to 35° C. to separate the water and oil phases. The oil phase is removed and dissolved in acetone such that oil is approximately 35% of the acetone-oil mixture. The mixture is then cooled to 10° C., filtered, the filtrate redissolved in acetone, and the process is repeated.

Erucic acid may exist either as a glyceride, where the diglyceride is dierucin and the monoglyceride is monerucin, or as the free fatty acid, and may be used in either form. In instances where the free fatty acid is preferred, the acid may be removed from the glycerol by any conventional means, such as, for example, the addition of a sodium hydroxide solution.

Erucic acid has utility for a number of applications. It is a raw material in the oleochemical industry for the synthesis of biodegradable lubricants and slip agents in the plastics industry. It also may be used for textile fiber lubrication (e.g., fabric softeners) and in hair care products.

The following examples are intended only to further illustrate the invention and are not intended to limit the scope of the invention which is defined by the claims.

EXAMPLES

Example 1

Production of Erucic Acid from HEAR Oil
Utilizing Lipase from *Geotrichum candidum*

Samples of HEAR oil (5 g) were stirred magnetically at 600 rpm with 3.5 ml of 50 mM phosphate buffer, pH 7, in which was dissolved 100 mg of lipase powder from *G. candidum*. Stirring took place in a stoppered, flat bottom glass tube, 3 cm×5 cm, which was placed in a glass mantle. The reaction temperature was maintained at 35° C. by circulating water from a constant temperature water-bath through the mantle. After a reaction time of 48 hours, the reaction mixture was heated to 35° C., resulting in the separation of the water and oil phases. The oil phase was removed, dissolved in about 15 ml of acetone and placed at 10° C. overnight. Crystals appeared during the cooling process and were separated from the acetone phase by filtering onto filter paper with a Büchner funnel. After the first filtration, the crystals were redissolved in about 15 ml fresh acetone, and the process was repeated.

Example 2

Production of Erucic Acid from HEAR Oil
Utilizing Lipase from *Candida rugosa*

Samples of HEAR oil (5 g) were stirred magnetically at 600 rpm with 3.5 ml of 50 mM phosphate buffer, pH 7, in which was dissolved 100 mg of lipase powder from *C. rugosa*. Stirring took place in a stoppered, flat bottom glass tube, 3 cm×5 cm, which was placed in a glass mantle. The reaction temperature was maintained at 10° C. by circulating water from a constant temperature water-bath through the mantle. After a reaction time of 48 hours, the reaction mixture was heated to 35° C., resulting in the separation of the water and oil phases. The oil phase was removed, dissolved in about 15 ml of acetone and placed at 10° C. overnight. Crystals appeared during the cooling process and were separated from the acetone phase by filtering onto filter paper with a Büchner funnel. After the first filtration, the crystals were redissolved in about 15 ml fresh acetone, and the process was repeated.

I claim:

1. A method for the enzymatic production of a glyceride consisting essentially of erucic acid, said method comprising
   a) dissolving lipase in water or buffer,
   b) adding the dissolved lipase to an erucic acid-containing sample, with stirring, to form a reaction mixture,
   c) incubating the reaction mixture for a time sufficient for the hydrolysis of fatty acids other than erucic acid to occur, thereby forming a glyceride fraction consisting essentially of erucic acid and a free fatty acid fraction,
   d) separating the glyceride fraction from the free fatty acid fraction, wherein the glyceride is dierucin or monoerucin, wherein the lipase is *Geotrichum candidum* lipase or *Candida rugosa* lipase, and wherein the reaction is carried out at a temperature of from about 10° C. to less than about 20° C. when the lipase is *Candida rugosa*.

2. The method of claim 1, wherein the lipase is *Geotrichum candidum* lipase, and the reaction is carried out at a temperature of about 10° C. to about 35° C.

3. The method of claim 2, wherein the reaction is carried out at a temperature of about 20° C. to about 35° C.

4. The method of claim 3, wherein the reaction is carried out at a temperature of about 35° C.

5. The method of claim 1, wherein the reaction is carried out at a temperature of about 10° C. when the lipase is *Candida rugosa* lipase.

6. The method of claim 1, wherein the water is present in the reaction mixture in an amount of at least 5 wt %.

7. The method of claim 1, wherein the reaction is carried out from about 2 hours to about 48 hours.

8. The method of claim 1, wherein the lipase is present in the reaction mixture in an amount of from about 0.2 wt % to about 8.0 wt %.

9. The method of claim 8, wherein the lipase is present in the reaction mixture in an amount of about 0.2 wt % to about 2.0 wt %.

10. The method of claim 9, wherein the lipase is present in the reaction mixture in an amount of about 0.2 wt %.

* * * * *